Figure 6:
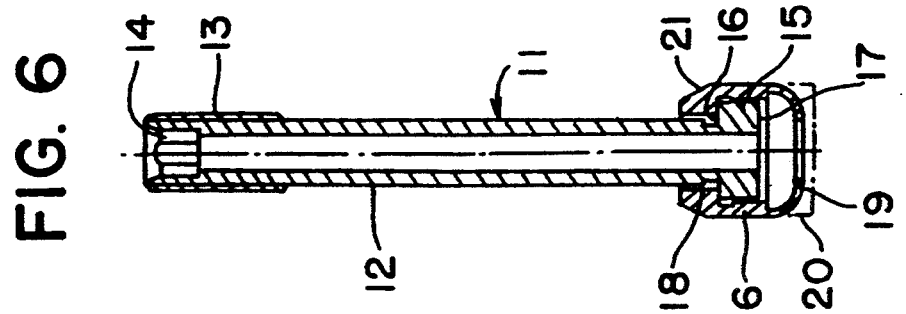

United States Patent [19]
Seidel et al.

[11] Patent Number: 5,441,500
[45] Date of Patent: Aug. 15, 1995

[54] BONE NAIL

[75] Inventors: Hartmut R. A. Seidel, Hamburg; Andreas W. Speitling, Kiel, both of Germany

[73] Assignee: Howmedica GmbH, Schoenkirchen, Germany

[21] Appl. No.: 828,400

[22] Filed: Jan. 30, 1992

[30] Foreign Application Priority Data

Jan. 30, 1991 [DE] Germany .................. 9101035 U

[51] Int. Cl.⁶ .................................. A61B 17/56
[52] U.S. Cl. ............................... 606/67; 606/68
[58] Field of Search ............... 606/61, 62, 63, 64, 606/65, 66, 67, 68, 72, 73

[56] References Cited

U.S. PATENT DOCUMENTS

| | | | |
|---|---|---|---|
| 2,381,050 | 8/1945 | Hardinge | 606/65 |
| 3,759,257 | 9/1973 | Fischer | 606/63 |
| 3,760,802 | 9/1973 | Fischer | 606/63 |
| 3,779,239 | 12/1973 | Fischer | 606/63 |
| 3,986,504 | 10/1976 | Avila | 606/63 |
| 4,013,071 | 3/1977 | Rosenberg | 606/73 |
| 4,091,806 | 5/1978 | Aginsky | 606/63 |
| 4,790,304 | 12/1988 | Rosenberg | 606/72 |
| 4,858,602 | 8/1989 | Seidel | 606/62 |
| 5,112,333 | 5/1992 | Fixel | 606/62 |

FOREIGN PATENT DOCUMENTS

| | | |
|---|---|---|
| 2141020 | 1/1973 | France . |
| 2542263 | 3/1977 | Germany . |
| 3146065 | 5/1983 | Germany . |

*Primary Examiner*—Michael A. Brown
*Attorney, Agent, or Firm*—Peter C. Richardson; Lawrence C. Akers; Elizabeth O. Slade

[57] ABSTRACT

A bone nail for upper arm fractures, including a hollow first shank adapted to be inserted into the proximal end portion of a medullary canal, the first shank having a distal end that has a slotted portion provided with a plurality of slots and an internal thread extending beyond the slotted portion.

1 Claim, 2 Drawing Sheets

FIG. 1
FIG. 2
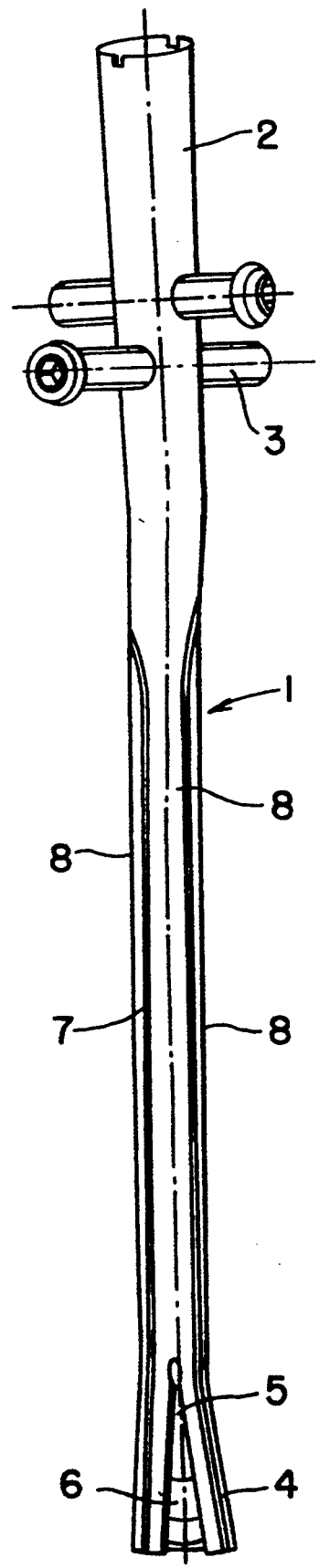
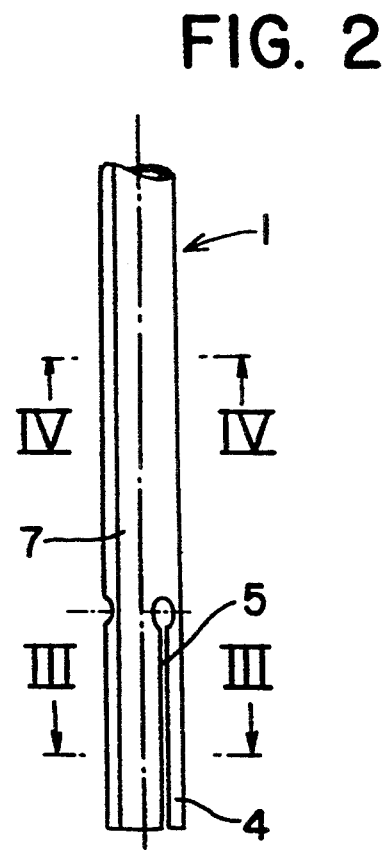

BONE NAIL

The invention refers to a bone nail for upper arm fractures, comprising a hollow shank adapted to be inserted in the proximal portion of the medulary canal, the shank having a distal end being provided with a plurality of slots and an internal thread beyond the slotted portion, the end comprising a threaded element having a shank with a threaded portion cooperating with the Internal thread and having further an expansion body in its head portion, the expansion body being drawn into this shank and expanding the slotted portion radially upon a rotation of the threaded element.

A threaded element of the kind mentioned above having a threaded portion cooperating with an internal thread of a nail shank and engaging elevations at the internal circumference of the shank has become known from EP-B-0 226 701. The expansion body is defined by the head of the threaded element and tapers conically towards the shank of the threaded element. Upon turning in the threaded element by a tool at the free end of the threaded element the head expands the slotted end of the shank radially whereby a dowel joint with the bone is achieved. During the expansion the head rotates along the inner circumference of this shank and the elevations which define an inner radius decreasing from the distal to the proximal end. The tuning in torque of the threaded element is substantially determined by a friction torque acting on the head which engages the elevations pointlike. The high torque is detrimental to the expansion of the distal nail end and may cause a change of the position of the nail. Furthermore the control of the expanding progress and thus of the expansion force exerted on the bone by the surgeon is effected. Also the release of the threaded element and the control thereof Is worsened. If the head slides on the elevations of the nail the control of the progress of the expansion can be disturbed by irregular oscillations of the torque.

With the invention, an improved bone nail is to be created which allows an improved control of the progress of the expansion with a reduced and more constant torque on the expansion element.

In the invention, the expansion body is supported by the head of the threaded element for rotation relative to said element.

Also with the bone nail according to the invention the expansion body which preferably tapers towards the shank of the threaded element is axially displaced along the shaft so that upon being drawn into the shank an expansion of the slotted end is effected as well as the radial contraction upon moving of the expansion body out of the shank. Contrary to the known bone nail the expansion body is rotatable relative to the head of the threaded element. If the threaded element is drawn against the shank the head does not rotate, rather moves only in the direction of this shank. Therefore an additional and occasionally irregular torque due to a rotation of an expansion body is avoided. Rather a friction torque is generated due to the support on the head, but this can be held relatively small by suitable shaping and dimensioning of the support surfaces because the friction force acts relatively near to the shank axis. The head of the threaded element can be defined by a step formed at the shank of the threaded element for the support of the expansion body. Maintaining an unequal tightening torque of the threaded element a considerably increased release torque is obtained according to the invention over a conventional nail. Due to the significantly reduced portion of the friction torque with respect to the tightening torque the surgeon can control the progress of the expansion more easily and may stop the process without damaging the bone if the nail is sufficiently dowled.

According to a preferred embodiment of the invention the expansion body has a radially inwardly projecting support surface which engages the rear end of the head facing the shank of the threaded element, wherein the expansion body is securely held between the head and the shank of the element.

In order to secure that the expansion body is urged out of the end portion of the nail upon releasing the threaded element, the body has a radially inwardly projecting edge which engages the front end of the head facing away from the shank of the element according to a preferred embodiment of the invention, the edge preferably being defined by a crimp forming. If the threaded element is released the head forces to take the expansion body with it so that the dowling is securely cleared. The crimp forming of the edge is relatively easy to be manufactured.

Preferably the head of the threaded element has a clearance between the projecting edge and the support surface of the expansion body such that a clamping-free rotation is achieved. Furthermore, the axial clearance allows a release of the threaded element by two "steps" wherein first the pre-stress of the threaded element is released and thereafter the pre-stress on the expansion body is removed after overcoming the clearance.

According to a further embodiment of the invention, the expansion body is guided at the circumference of the element, preferably by the circumference of the head without a clearance. This helps drawing-in the expansion body in the opened end portion of the nail without the lower edge being supported on the front edge of the nail.

Preferably, the head of the threaded element is cylindrical thereby obtaining a large support surface on the rear end and a corresponding guiding surface on the circumference.

For a secure drawing-in of the expansion body into the distal nail opening and for a significant spreading of the slotted nail end the expansion body can be provided with a cone which tapers towards the shank of the element. Particularly the hollow shank may have elevations and indentations alternating in circumferential direction whereby the inner radius in the slotted shank portion defined by the elevations reduces from the distal to the proximate end of the shank.

Finally, an embodiment of the invention provides an expansion body of stainless steel, in particular of implantable chromium nickel steel or of another material suited for implantation.

Further details and advantages of the subject matter of the invention can be derived from the description below in connection with associated drawings which illustrate a preferred nail according to the invention.

Figure 5:
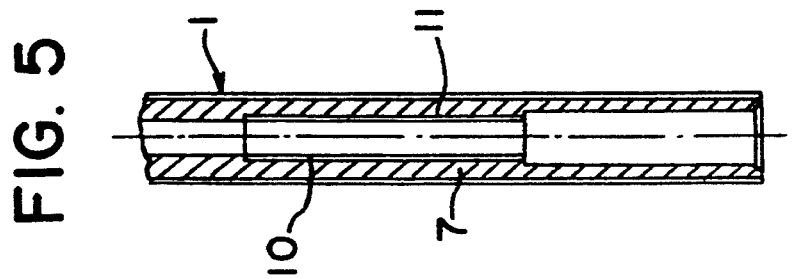
Figure 4:
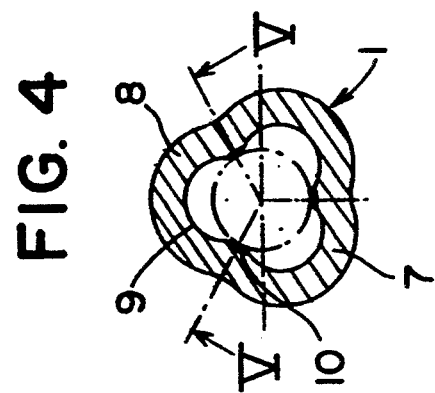
Figure 3:
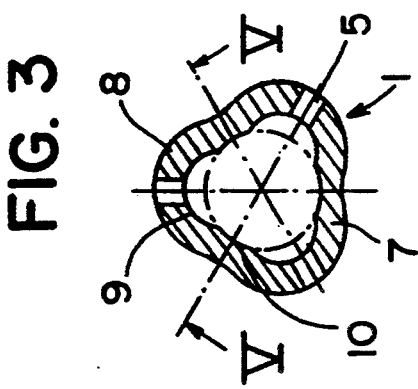

FIG. 1 is a side view of a bone nail according to the invention with an expanded distal end FIG. 2 is a side view of the distal end of the bone nail of FIG. 1 in the non-expanded state FIG. 3 is a cross section of the bone nail of FIG. 2 along line III—III FIG. 4 is a cross section of the bone nail of FIG. 2 along line IV—IV FIG. 5 is a cross section through the bone nail of FIG. 3 or 4 along III—III or IV—IV FIG. 6 is a longitudinal section of a threaded element with an expansion body for the expansion of the distal nail end FIG. 1 illustrates a bone nail 1 which has transverse screws 3 near the proximate end 2 for the interlocking with a bone (not shown). A distal end 4 of the bone nail 1 is provided with longitudinal slots 5 and can be expanded radially by an expansion body 6 which is threaded into the distal end. Shank 7 of nail 1 has three elevations 8 circumferentially spaced.

As can be seen in FIG. 2 the distal end of nail 1 is aligned parallel with respect to the shank 7 if no expansion body is inserted.

From FIGS. 3 and 4 it can be seen that the elevations 8 at the outer circumference correspond to depressions 9 at the inner circumference of shank 7, with elevations 10 being located between the depressions. It can be further seen that the inner diameter defined by the elevation 10 at the inner circumference decrease from the distal end 4 of nail 1 to its proximate end. FIG. 4 illustrates in connection with FIG. 5 that the elevations 10 of shank 7 have an internal thread 11a.

A similar threaded element is known from EP-0 226 701 which can be provided with a proximal clip having spider-shaped arms instead of locking washers.

In order to expand the nail I a threaded element 11 shown in FIG. 6 can be turned into the nail 1, wherein a shank 12 of the element has an enlarged diameter at one end provided with a threaded portion 13. The threaded portion 13 cooperates with the internal thread 11a of nail 1. An internal hexagon 14 is formed in the same end of shank 12 into which a tool can be inserted through the proximate end 2 of nail 1.

At the other end, the shank 12 has a cylindrical head 15 including a rear end 16 facing shank 12 and a front end 17 facing away from shank 12.

A disk-like spreading body 6 engages the rear end 16 of the head 15 by a radially inwardly projecting support surface 18, the clearance between the expansion body 6 and the circumference of head 15 being only some tenth millimeters. The expansion body 6 overlaps the front end 17 of the head by a crimped portion 19 which is produced by a deformation of a edge 20 shown in dash-dotted lines. Thus, the head 15 has an axial clearance between the support surface 18 and the crimped portion 19.

Finally, the expansion body 6 has an outer cone 21 tapering towards the shank 12.

The outer diameter of the expansion body 6 corresponds approximately to that of the undeformed shank 7 of the nail 1 and is for example 9 or 11 mm. Turning the element 11 into the distal end 4 of the nail 1 the threaded element 11 expands radially the distal end, wherein the cone 21 allows a large expansion range in conjunction with the elevations. With an outer shank diameter of 9 mm an expansion of for example 18 mm can be achieved.

In expanding the rear end 16 of the head smoothly slides on the support surface 18 of the expansion body 6 which does not rotate due to the friction forces acting on cone 21. Turning out the screw the crimped portion 19 causes the expansion body to be taken along with. In a most simple case the expansion body 6 consists of a washer.

We claim:
1. A bone nail for upper arm fractures, comprising
(a) A hollow first shank adapted to be inserted into the proximal end portion of a medullary canal, said first shank having a distal end having a slotted portion provided with a plurality of slots and an internal thread extending beyond said slotted portion; and
(b) A threaded element having
  (1) a second shank with a threaded portion cooperating with said internal thread and having further
  (2) a head portion having an expansion body, said expansion body being able to be drawn into said first shank and expanding said slotted portion radially upon a rotation of said threaded element, wherein said expansion body is rotatably supported by said head portion of said threaded element so as to allow rotation of said expansion body relative to said threaded element and wherein said expansion body is axially secured relative to said threaded element so as to prevent axial movement of said expansion body relative to said threaded element upon rotation of said threaded element,
wherein said expansion body has a radially inwardly extending support surface which engages the rear end of said head facing said second shank of said threaded element, wherein said expansion body has a radially inwardly projecting edge, preferably a crimped portion, which overlaps the front end of said head facing away from the shank of said threaded element, wherein said head of said threaded element is located between said projecting edge and said support surface of said expansion body with an axial clearance, wherein said expansion body is guided along the circumference of said threaded element, preferably along the circumference of said head, with a small clearance, wherein said head of said threaded element is cylindrical, wherein said expansion body has an outer cone which tapers towards said shank of said threaded element, and wherein said hollow shank has alternating internal elevations and depressions, and wherein the inner radius defined by said elevations in said slotted portion of said shank decreases from the distal to the proximal end.

* * * * *